(12) United States Patent
Tomer et al.

(10) Patent No.: US 11,266,642 B2
(45) Date of Patent: Mar. 8, 2022

(54) SMALL MOLECULE INHIBITORS OF HLA-DR3 BINDING FOR TREATING AUTOIMMUNE THYROIDITIS

(71) Applicant: ICAHN SCHOOL OF MEDICINE AT MOUNT SINAI, New York, NY (US)

(72) Inventors: Yaron Tomer, New York, NY (US); Roman Osman, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 734 days.

(21) Appl. No.: 16/063,942

(22) PCT Filed: Dec. 20, 2016

(86) PCT No.: PCT/US2016/067775
§ 371 (c)(1),
(2) Date: Jun. 19, 2018

(87) PCT Pub. No.: WO2017/112669
PCT Pub. Date: Jun. 29, 2017

(65) Prior Publication Data
US 2020/0281919 A1    Sep. 10, 2020

Related U.S. Application Data

(60) Provisional application No. 62/270,870, filed on Dec. 22, 2015.

(51) Int. Cl.
*A61K 31/4725* (2006.01)
*A61P 37/02* (2006.01)

(52) U.S. Cl.
CPC .......... *A61K 31/4725* (2013.01); *A61P 37/02* (2018.01)

(58) Field of Classification Search
CPC ..................... A61K 31/4725; A61P 37/02
See application file for complete search history.

(56) References Cited

U.S. PATENT DOCUMENTS

| | | |
|---|---|---|
| 2011/0039756 A1 | 2/2011 | Hammerli et al. |
| 2015/0190392 A1 | 7/2015 | Wong et al. |
| 2015/0202285 A1 | 7/2015 | Thomas et al. |

OTHER PUBLICATIONS

Schiff, Jr., The Bisbenzylisoquinoline Alkaloids—A Tabular Review, Chapter One of the Book "Alkaloids: Chemical & Biological Perspectives", vol. 14, Ed. S. William Pelletier, Pergamon, 1999.

International Search Report & Written Opinion issued in PCT/US2016/067775, dated Mar. 10, 2017.
Lee, Hanna J., et al., "Immunogenetics of Autoimmune Thyroid Diseases: A Comprehensive Review" Journal of Autoimmunity, vol. 64, p. 6, lines 82-90 (Nov. 2015).
Li, Cheuk Wun, et al., "Identifying a Small Molecule Blocking Antigen Presentation In Autoimmune Thyroiditis" Journal of Biological Chemistry, vol. 291, pp. 4079-4090 (Dec. 24, 2015).
Database Registry [Online] Chemical Abstracts Service, Columbus, Ohio, US; Database Accession No. 1350227-24-5, XP002792980 Dec. 7, 2011.
Database Registry [Online] Chemical Abstracts Service, Columbus, Ohio, US; Database Accession No. 1349781-60-7, XP002792981 Dec. 6, 2011.
Uto, et al., Inhibitory effect of 1-7 cepharanthine on dendritic cell activation and function, International Immunopharacology, Elsevier Amsterdam NL, vol. 11, No. 11, pp. 1932-1938, XP028326779 Aug. 3, 2011.
Furusawa, et al., The effects of biscoclaurine alkaloid cepharanthine on mammalian cells: Implications for cancer, shock, and inflammatory diseases, Life Sciences, Pergamon Press, Oxford, GB, vol. 80, No. 12, pp. 1073-1079, XP005891963 Feb. 15, 2007.
Extended European Search Report in European Application No. 16879971.6 dated Jul. 31, 2019.
Kondo, et al., Selective Inhibition of T-Cell-Dependent Immune Responses by Bisbenzylisoquinoline Alkaloids In Vivo, Int. J. Immunopharmac., vol. 14, No. 7, pp. 1181-1186 1992.

*Primary Examiner* — Alicia L Otton
(74) *Attorney, Agent, or Firm* — Heslin Rothenberg Farley & Mesiti, P.C.

(57) ABSTRACT

A method for treating autoimmune thyroid disease is disclosed. The method comprises administering a molecule of molecular weight below 700 that inhibits the binding of the nonadecapeptide IPDNLFLKSDGRIKYTLNK (SEQ ID NO:1) to HLA-DRβ1-Arg74. Such compounds are found in the class of bisbenzylisoquinoline alkaloids represented by formula I

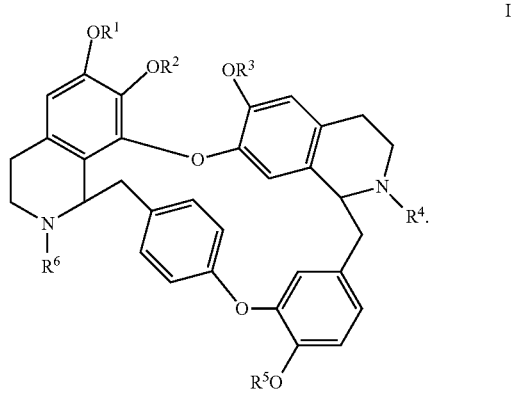

12 Claims, No Drawings
Specification includes a Sequence Listing.

SMALL MOLECULE INHIBITORS OF HLA-DR3 BINDING FOR TREATING AUTOIMMUNE THYROIDITIS

CROSS REFERENCE TO RELATED APPLICATIONS

This application is a U.S. National Phase filing under 35 U.S.C. § 371 of International Application PCT/US2016/067775, filed Dec. 20, 2016, and published as WO 2017/112669 on Jun. 29, 2017. PCT/US2016/067775 claims priority from U.S. provisional application 62/270,870, filed Dec. 22, 2015. The entire contents of each of the prior applications are incorporated herein by reference.

FEDERALLY SPONSORED RESEARCH

This invention was made with Government support under DK061659, DK073681, and T32 AI007605 awarded by the National Institutes of Health. The Government has certain rights in the invention.

FIELD OF THE INVENTION

The invention relates to the use of small molecule inhibitors of HLA-DRβ1-Arg74, which are useful to treat autoimmune thyroid disease, particularly Hashimoto's Thyroiditis and Grave's disease.

BACKGROUND

Autoimmune thyroid diseases (AITD), including Graves' disease (GD) and Hashimoto's thyroiditis (HT), are among the most common autoimmune disorders, afflicting up to 5% of the US population. They are characterized by infiltration of the thyroid by lymphocytes reactive to thyroid antigens and production of thyroid-specific antibodies. Complex interaction of genetic susceptibility factors, environmental triggers, and epigenetic alterations leads to the breakdown of tolerance, resulting in autoimmune thyroid diseases. Currently, there is no satisfactory therapy except for hormone replacement therapy in Hashimoto's thyroiditis or thyroid suppression or ablation in Graves' disease. We have identified a specific HLA-DR pocket sequence that is strongly associated with autoimmune thyroid disease. The presence of arginine at position 74 of the DRβ chain renders the individual highly susceptible to autoimmune thyroid diseases, while glutamine at position 74 is protective. The presence of DRβ1-Arg74 (from here on we refer to the HLA-DR3 containing arginine at position 74 as HLA-DRβ1-Arg74) results in a more positively charged P4 pocket. With this structural change in the pocket, the selectivity and binding of pathogenic peptides is affected, conferring higher risk for disease activation.

Besides the HLA genes, two thyroid-specific genes, the thyroglobulin (Tg) and thyrotropin receptor (TSHR) genes also contribute to the etiology of autoimmune thyroid disease. Thyroglobulin is the most abundant thyroidal protein, and it is the precursor to thyroid hormones T3 and T4. All forms of autoimmune thyroid disease (including both Grave's disease and Hashimoto's thyroiditis) are characterized by the development of Tg antibodies in the majority of patients, and mouse data suggest that Tg is the primary target of the autoimmune response in autoimmune thyroid disease. Jacobson et al. [*J Biol Chem* 284, 34231-34243 (2009)] showed that the DRβ1Arg74 pocket facilitates the presentation of pathogenic Tg peptides to T-cells and identified four peptides (Tg.1951, Tg.2098, Tg.1571, Tg.726) that showed strong and specific binding to DRβ1-Arg74 but much weaker binding to the protective-Gln74.

In view of the important interaction between these Tg peptides and the HLA-DRβ1-Arg74 peptide binding pocket, the person of skill will recognize that blocking the presentation of these peptides to autoreactive T-cells that escaped tolerance could be used to treat autoimmune thyroid disease. Such a targeted therapy could prevent the continuous activation of T-cells against thyroid antigens that is necessary to maintain the autoimmune response in autoimmune thyroid disease and might reverse it. Described herein are small molecule inhibitors that can block Tg peptide presentation by HLA-DRβ1-Arg74 as a potential new treatment modality for autoimmune thyroid disease.

SUMMARY OF THE INVENTION

In one aspect the invention relates to a method for treating, forestalling or reducing the risk of autoimmune thyroid disease comprising administering to a patient a compound of formula I

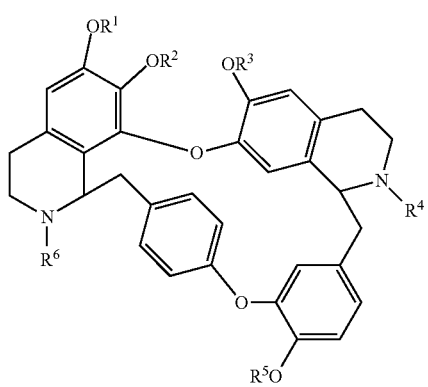

wherein $R^1$ and $R^2$ are chosen independently from H and $CH_3$, or, taken together $R^1$ and $R^2$ are $-CH_2-$; and $R^3$, $R^4$, $R^5$, $R^6$ are chosen independently from H and $CH_3$.

In another aspect, the invention relates to a method for treating autoimmune thyroid disease comprising administering to a human a molecule of molecular weight below 700 that inhibits the binding of the nonadecapeptide IPDNLFLKSDGRIKYTLNK (SEQ ID NO:1) to HLA-DRβ1-Arg74 with an $IC_{50}$ below 100 nM in the In Vitro Arg74 Blocking Test described below.

DETAILED DESCRIPTION OF THE INVENTION

Substituents are generally defined when introduced and retain that definition throughout the specification and in all independent claims.

Compounds of the invention fall into the genus of bis-benzylisoquinoline alkaloids. These alkaloids are well known and are derived from widely diverse plant sources. Of particular interest is cepharanthine, formula Ia

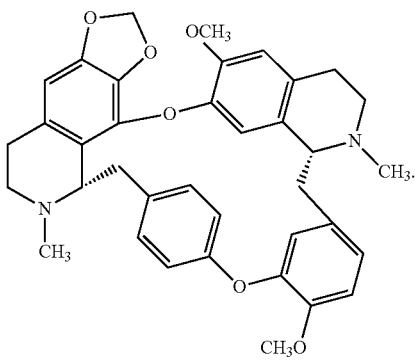

Ia

Other members of the class include cycleapeltine, demerarine, seeperine, johnsonine, repandine, O-methylrepandine, norcepharanthine 2-norisocepharanthine, gyrolidine, gyrocarpine, macolidine, and oxyacanthine.

As used herein, and as would be understood by the person of skill in the art, the recitation of "a compound"—unless expressly further limited—is intended to include salts of that compound. Thus, for example, the recitation "a compound of formula"

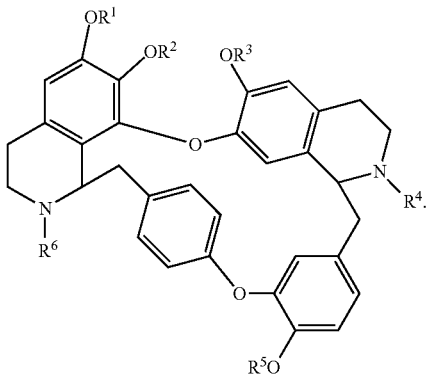

as depicted above would include salts in which either or both of the tetrahydroisoquinoline nitrogens is protonated, for example:

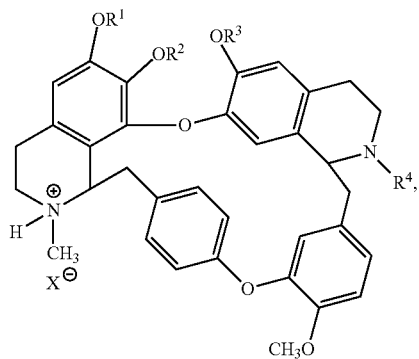

wherein $X^-$ is any counterion. In a particular embodiment, the term "compound of formula I" refers to the compound or a pharmaceutically acceptable salt thereof. Unless otherwise stated, structures depicted herein are also meant to include all stereoisomeric (e.g., enantiomeric, diastereomeric, and cis-trans isomeric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and cis-trans isomeric (or conformational) mixtures of the present compounds are within the scope of the invention. Unless otherwise stated, all tautomeric forms of the compounds of the invention are within the scope of the invention.

Also provided herein is a pharmaceutical composition comprising a compound of formula (I), or a pharmaceutically acceptable salt form thereof, and a pharmaceutically acceptable carrier or diluent.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

While it may be possible for the compounds of formula (I) to be administered as the raw chemical, it is preferable to present them as a pharmaceutical composition. According to a further aspect, the present invention provides a pharmaceutical composition comprising a compound of formula (I) or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^{2}H$, $^{3}H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^{3}H$, and carbon-14, i.e., $^{14}C$, radioisotopes are particularly preferred for their ease in preparation and detectability. Compounds that contain isotopes $^{11}C$, $^{13}N$, $^{15}O$ and $^{18}F$ are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The compounds provided herein can be used for treating autoimmune thyroid diseases in a patient, the method comprising administering to the patient a therapeutically effective amount of a compound described herein, or a pharmaceutically acceptable salt form thereof. In some situations it may be advantageous to screen the patient population for those patients that carry an HLA-DRβ1-Arg74 variant. This may indicate an increase in the benefit of the instant therapeutic agents to such individual patients.

Unless defined otherwise, all technical and scientific terms used herein have the same meaning as is commonly understood by one of ordinary skill in the art to which this disclosure belongs. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference. In the event that there is a plurality of definitions for terms cited herein, those in this section prevail unless otherwise stated.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof, but only if the additional features, integers, steps, components or groups thereof do not materially alter the basic and novel characteristics of the claimed composition or method.

A "patient," as used herein, includes both humans and other animals, particularly mammals. Thus the methods are applicable to both human therapy and veterinary applications. In some embodiments, the patient is a mammal, for example, a primate. In some embodiments, the patient is a human.

Treatment can involve administering a compound described herein to a patient diagnosed with a disease, and may involve administering the compound to a patient who does not have active symptoms. Conversely, treatment may involve administering the compositions to a patient at risk of developing a particular disease, or to a patient reporting one or more of the physiological symptoms of a disease, even though a diagnosis of this disease may not have been made.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease. A therapeutic benefit is achieved with the amelioration of one or more of the physiological symptoms associated with the underlying disorder such that an improvement is observed in the patient, notwithstanding that the patient may still be afflicted with the underlying disorder.

The term "inhibit" with respect to a small molecule's effect on the binding of a peptide to HLA-DRβ1-Arg74 refers to diminution of the binding that is statistically significant. Compounds that exhibit an $IC_{50}$ below 100 nM in the DELFIA immunoassay utilizing the APO peptide/HLA-Dβ1-Arg74 binding protocol described below are preferred.

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in *Protecting Group Chemistry*, 1st Ed., Oxford University Press, 2000; and in *March's Advanced Organic chemistry: Reactions, Mechanisms, and Structure*, 5th Ed., Wiley-Interscience Publication, 2001.

Many compounds of the invention can be obtained commercially. Others may be synthesized by procedures described in the art or variations thereon employing analogous starting materials. Compounds were purchased from Chembridge (San Diego, Calif.) or from Microsource Discovery Systems (Gaylordsville, Conn.). Cepharanthine analogs may be obtained from extracts of *Stephania pierii*, *Abuta grisebachi*, *Colubrina faralaotra*, and numerous other plant sources described in *Alkaloids: Chemical and Biological Perspectives*, vol 14, S. W. Pelletier editor, pages 200-204 (2004) and *The Alkaloids: Chemistry and Pharmacology*, vol 41, A. Brossi and G. A. Cordell editors, pages 1-40 (1992), both of which are incorporated herein by reference.

Three peptides used in this study, Tg.2098, SCR2098, and APO were synthesized by Genscript (Piscataway, N.J.).) The sequences of the peptides are:

```
Tg.2098:
                                          (SEQ ID NO: 2)
LSSVVVDPSIRHFDV

APO:
                                          (SEQ ID NO: 1)
IPDNLFLKSDGRIKYTLNK scr2098:
                                          (SEQ ID NO: 3)
HDLFSRIDSSVVVVP
```

HLA-DRβ1-Arg74 protein (containing arginine at position 74 on the β chain) was produced using the baculovirus system. We designed 2 constructs for both the α and β chains of HLA-DR. The β-chain construct contained the extracellular portion of the DRB1*0301 β chain fused to the coiled coil region of the basic Leucine zipper domain of JunB, and the α chain construct contained the extracellular portion of the DR α chain fused to the coiled coil region to the basic Leucine zipper domain of Fos. A TEV protease cutting site was introduced in each chain to allow removal of the dimerization motif. The JunB and Fos dimerization motifs allowed the protein to dimerize and form the final HLA-DRβ1-Arg74 protein. These constructs were used to produce the HLA-DRβ1-Arg74 protein in a Baculovirus system using the Life Technologies Baculovirus protein production custom services (Carlsbad, Calif., USA).

Test compounds were dissolved in 100% DMSO and tested for their ability to bind to the HLA-DRβ1-Arg74 pocket and block it from binding the peptide using an immunoassay we developed for this purpose, which will be referred to as the "In Vitro Arg74 Blocking Test". In order to test whether a test compound blocked the Arg74 pocket, we used the recombinant HLA-DRβ1-Arg74 protein generated as described above and the apopeptide (APO), IPDNLFLKSDGRIKYTLNK (SEQ ID NO:1), a peptide that was previously shown to be the best binder to this pocket. In this assay 0.012 mg/mL HLA-DRβ1-Arg74 protein was incubated with 10 μM biotinylated APO (Genscript, Piscataway, N.J.), together with 0.2-0.4 mM of the tested small molecule, for 48 h at 37° C. in binding buffer (0.1% BSA/PBS with 0.05% Triton [PBST] Aldrich, St. Louis, Mo.). On the day before the immunoassay was performed, a 96-well DELFIA yellow plate (PerkinElmer) was coated overnight with 20 μg/mL of L243 antibody (Hybridoma was purchased from ATCC, Catalog no. HB-55 and IgG was purified by QED Bioscience, San Diego, Calif.) in bicarbonate buffer pH 9.6 (Sigma-Aldrich). L243 is a monoclonal antibody that specifically recognizes the DRα chain when it is properly folded and complexed with the β chain [Fu et al. Hum Immunol, 36, 253-260 (1994)]. The plate was then washed with DELFIA wash buffer (diluted 1:25 from DELFIA Wash Concentrate, PerkinElmer) to wash off the excess L243 antibody. Blocking was done using 2.5% BSA in PBS at room temperature for 1 h. After washing 4 times, 100 μL of the pre-incubated complex (HLA-DRβ1-Arg74 protein-APO-small molecules) were added onto the plate and shaken at slow speed for 2 h at room temperature. After washing 4 times, DELFIA Eu-labeled Streptavidin (PerkinElmer) diluted in DELFIA assay buffer (PerkinElmer) was added for 30 min and shaken at slow speed at room temperature. After washing 6 times, DELFIA Enhancement Solution was added for 1 h or until optimal signal was reached. Time-resolved fluorescence was measured using the BMG reader (BMG Labtech, Cary, N.C.). The experiment was performed in triplicates. Biotinylated APO peptide that was not pre-incubated with HLA-DRβ1-Arg74 was added as negative control. Percent inhibition was calculated by the following formula: 100−100×[HLA-DRβ1-Arg74-APO-small molecule/HLA-DRβ1-Arg74-APO (no small molecule)])

To gauge the potency of the small molecules we determined the percent inhibition at decreasing concentrations of test molecules. Compound Ia was serially diluted to 0.0125 mM final concentration from an initial concentration of 0.2 mM and incubated with the HLA-DRβ1-Arg74-APO complex for 48 h at 37° C. for assessing the percentage of inhibition. Immunoassay was performed as described above. Compound Ia inhibited APO binding to HLA-DRβ1-Arg74 in a dose-dependent manner, with approximate IC50 of 0.08 mM.

VAVY cells (European Collection of Cell Cultures) were cultured in RPMI (ATCC, Manassas, Va.) supplied with 10% FBS (Sigma-Aldrich, St. Louis, Mo.), 1% Penicillin-Streptomycin (Corning, N.Y.), 2 mM glutamine (Corning, N.Y.) and 5 mg ciprofloxacin hydrochloride (Hospira, Lake Forest, Ill.). Cells were grown at 37° C., 5% $CO_2$ and passaged 1-2 times a week. Cells expressing DR2 (National Development and Research Institutes, Inc) were cultured using the same conditions as VAVY cells.

N-terminal biotinylated peptide Tg.2098 was used to test for binding to VAVY cells which express HLA-DR3 on their surface (HLA-DRβ1-Arg74 positive). APC Streptavidin (BD Biosciences, Franklin Lakes, N.J.) was used to detect the biotinylated peptides. A scrambled peptide of Tg.2098 (scr2098) was used as a negative control. VAVY cells were seeded at 2.5×10⁶ cells/mL in a 24-well plate (BD Biosciences) and pre-incubated for 7 hours with 0.025 mM of compound Ia or 40% Captisol (Ligand Pharmaceuticals, Inc, La Jolla, Calif.) [the vehicle used to dissolve test compound in this experiment], before 0.5 μM Tg.2098 was added. After 24 h incubation, cells were stained with PE mouse anti-human HLA-DR (BD Biosciences) and APC Streptavidin to detect binding of the peptide to VAVY cells and the inhibitory effect of Compound Ia. Inhibition was analyzed by flow cytometry. As a negative control, cells expressing HLA-DR2 were pre-incubated with example Ia or 40% Captisol, before biotinylated myelin basic protein (MBP) 87-99 (known binder to HLA-DR2) was added and incubated for 24 hours. HLA-DR2 cells were stained with PE mouse anti-human HLA-DR and APC Streptavidin to detect binding of biotinylated MBP87-99 to DR2 expressing cells and to assess the inhibitory effect of compound Ia on peptide binding.

To confirm the ELISA results we performed binding inhibition studies using the VAVY B-cell line that is homozygous for DR3 (confirmed to contain DRβ1-Arg74). Biotinylated Tg.2098 was incubated with VAVY cells in the presence of compound Ia (dissolved in 40% Captisol [Ligand Pharmaceuticals, Inc, La Jolla, Calif.] which is not toxic to cells) or in the presence of 40% Captisol alone (negative control). The binding of Tg.2098 to HLA-DR3-positive VAVY cells was 42.7% when incubated without Ia while the negative control peptide (scr.2098) showed 2.1% of binding to HLA-DR3-positive VAVY cells, confirming the specificity of Tg.2098 binding to HLA-DR3 (DRβ1-Arg74 positive) on VAVY cells. In the presence of 0.025 mM Ia, the binding of Tg.2098 to VAVY cells was reduced to 16.6%, confirming the ELISA results and suggesting that Ia can block the presentation of Tg.2098 within HLA-DR3 to T-cells. We confirmed that Ia blocked specifically the binding of peptides to DR3 and did not block other DR pockets by showing that Ia did not block the binding of MBP87-99 (known specific binder to DR2) from binding to DR2.

Mice transgenic for DRB1*0301 were originally generated by G. J Hämmerling and co-workers as previously described [Strauss et al. *Immunogenetics* 40, 104-108 (1994)]. Briefly, the DR3 (DRA1*0101/DRB1*0301) transgenes were inserted into (C57BL/6×DBA/2) F1 embryos and the progeny were back-crossed to B10.Q mice. The DR3 mice were crossed with I-Aβ knockouts (C57BL/6×129) to obtain mice lacking murine MHC class II and expressing human DR3. The transgenic mouse line was maintained by intercrossing. The background non-MHC genes in the DR3 transgenic line was 50% C57BL/10 genes and 50% contribution from CBA, C57BL/6, and 129 genes. These mice were then back-crossed into NOD background to produce the NOD-DR3 mice [Flynn et al. *J Autoimmun*, 17, 7-15 (2001)]. The transgene was confirmed to be HLA-DRβ1-Arg74 positive. Mice were bred in a pathogen-free facility (Icahn School of Medicine at Mount Sinai, New York, N.Y.), and expression of HLA-DR3 was tested by PCR using DR3-specific primers: forward primer 5' CGCTTCGACAGCGAC 3' (SEQ ID NO:4) and reverse primer 5' GACAAATCCACACTCCAC 3' (SEQ ID NO:5). DR3 transgenic mice on NOD background known to be susceptible to experimental immune thyroiditis (EAT) were used in this study.

Female NOD-DR3 mice, 4-6 weeks old, were injected subcutaneously with human thyroglobulin (hTg) (Cell Sciences, Canton, Mass.) in complete Freund adjuvant (CFA) (Sigma) to induce EAT. Mice were immunized with hTg on day 0 and boosted on day 7; mice were sacrificed on day 21. For some mice, PC61 (anti-CD25) antibody (ATCC) at 7.5 mg/mL was injected i.p. on day (−4) and day 3 to deplete T regulatory (CD25+) cells and augment the autoimmune response to hTg.

Spleen and draining lymph nodes were collected from mice upon sacrifice. The spleens and draining lymph nodes were harvested in complete RPMI (Corning) supplemented with 10% FBS (Sigma-Aldrich,) and 1 mM sodium pyruvate (Sigma-Aldrich). They were cut and pressed in circular motion using a plunger from a 10 mL syringe. The suspension was filtered through a 100 μm cell strainer twice and centrifuged at 200×g for 10 minutes. The supernatant was discarded. The pellet was washed with RPMI and centrifuged one more time. Five mL Ammonium-Chloride-Potassium (ACK) lysis buffer was added to remove erythrocytes from the spleen. After 5-min incubation with ACK lysis buffer at room temperature with occasional shaking, cells were centrifuged at 200×g for 10 min. The pellet was resuspended in RPMI and the cells were counted and plated.

Cells harvested from the spleen and lymph nodes were resuspended at $2 \times 10^6$ cells/ml in 0.1% BSA/PBS. $1 \times 10^6$ cells were labeled with 1.5 μM carboxyfluorescein diacetate, succinimidyl ester (CFSE) (Life Technologies). After incubating for 10 min at 37° C., the staining was terminated by the addition of 4 volumes of ice-cold RPMI/10% FBS. After 5 min of incubation on ice, the cells were washed 3 times with fresh RPMI and resuspended in fresh medium for counting.

The CFSE-labeled cells were plated at $2 \times 10^5$ cells per well in 100 μL of medium (RPMI/10% FBS). The cells were treated with medium, human thyroglobulin (40 μg/mL), Tg.2098 (20 μg/ml), the unrelated negative control peptide scr2098 (20 μg/ml), or mouse CD3/CD28 beads (Life Technologies) as positive control. The results from the unrelated negative control peptides were averaged. The cells were collected after 5 days for flow cytometry analysis. All experiments were performed in quadruplicates. The results were analyzed using Flowjo (Tree Star, Ashland, Oreg.). The stimulation index was calculated by using the following formula: Stimulation index=[% proliferating lymphocytes (hTg, peptide or mitogen-treated)]/[% proliferating lymphocytes (medium-treated)]. Tg.2098 showed a stimulation index which was similar to that of the hTg native protein.

Immunized mice splenocytes were incubated with hTg with or without compound Ia; as negative control the splenocytes were incubated with vehicle (DMSO) alone. Compound Ia (final concentration 0.001 mM) significantly blocked the activation of T-cells of hTg immunized mice by both hTg (p=0.0005, one-tailed t-test, paired) and by Tg.2098 (p=0.0079, one-tailed t-test, paired).

Immunized mice splenocytes were incubated with 1 μM compound Ia together with human thryroglobulin (40 μg/mL) or Tg.2098 (20 μg/mL) to assess the inhibition of cytokines production by compound Ia. To demonstrate the inhibition is specific, DMSO was used as a control. Milliplex mouse cytokines/chemokine magnetic panel (Catalog no. MCYTOMAG-70K, EMD Millipore Corporation, Billerica, Mass.) was used to assay the cytokines. Splenocytes were plated at $2 \times 10^6$ cells per well in 500 uL of medium (RPMI/10% FBS). Supernatants were collected 48 hours after stimulation with hTg or peptides and stored at −80° C. until the assay was performed. To begin the assay, the 96-well plate supplied in the kit was washed with the wash buffer supplied and the plate was shaken for 10 min at room temperature. Standards and quality controls were added, followed by the samples. The pre-mixed beads (IFN gamma, IL-2, IL-4, IL-10) were sonicated and vortexed, and then added to the wells. After shaking the plate overnight at 4° C., the plate was washed twice with wash buffer. Detection antibodies were added for 1 h at room temperature, and Streptavidin-Phycoerythrin was added for 30 min at room temperature. The plate was washed twice and sheath fluid was added to resuspend the beads for 5 min before reading in Luminex 200 with xPONENT software (Luminex, Austin, Tex.)

Tg.2098 induced the strongest cytokine responses in immunized NOD-DR3 mice that developed experimental autoimmune thyroiditis, again supporting Tg.2098 as a major hTg epitope. Interferon was inhibited by 38.7% when hTg was incubated with splenocytes from immunized mice together with Compound Ia (p=0.002, paired t-test, one-tailed) (Figure 13), and by 48.8% when Tg.2098 was incubated with splenocytes together with Compound Ia (p<0.0001, paired t-test, one-tailed).

One hundred percent of the immunized mice were positive for hTg antibodies at sacrifice, demonstrating that they all developed humoral responses, which are the most sensitive biomarker of EAT. These data demonstrate that Tg.2098 is a primary Tg epitope presented by HLA-DRβ1-Arg74. Ten out of fifteen NOD-DR3 mice injected with hTg showed varying degrees of thyroid lymphocytic infiltration. Ninety percent of mice that developed lymphocytic infiltration also had T-cell responses to Tg.2098.

The foregoing tests show that Compound Ia can block thyroglobulin peptide presentation by HLA-DR 1-Arg74 pockets and suppress T-cell activation by these Tg peptides.

Compound Ia was examined in vivo intraperitoneally administered and orally administered.

Seven female NOD-DR3 mice (6-10 weeks old) were injected IP with 125 of Compound Ia on day (−2) and day (−1), followed by SQ immunization of human thyroglobulin (hTg) mixed with CFA on day 0. Vehicle that was used to dissolve Compound Ia was injected in 5 female NOD-DR3 mice as a negative control. Mice were injected IP again with 125 µg of Compound Ia (or vehicle) on day 5 and day 6, followed by SQ immunization of hTg with CFA on day 7. Mice were sacrificed on day 21. Splenocytes and lymph node lymphocytes were isolated and incubated with hTg to test for their T-cell proliferative responses to this thyroid autoantigen. Splenocytes/lymphocytes were harvested 5 days after stimulation (with hTg) and assayed for T-cell proliferation using the CFSE assay on BD Accuri flow cytometer. The stimulation index was calculated by using the formula described above: Stimulation index=[% proliferating lymphocytes (hTg, peptide or mitogen-treated)]/[% proliferating lymphocytes (medium-treated)]. T-cell stimulation in response to hTg was significantly decreased in the group treated with Compound Ia (p=0.0432), as shown in Table 1

TABLE 1

| Vehicle plus hTg | Compound Ia plus hTg |
|---|---|
| 2.3 ± 0.5 | 1.3 ± 0.2 |

Three female NOD-DR3 mice (6 to 10 weeks old) were fed with 250 µg of Compound Ia PO using gavage on day (−2) and day (−1), followed by SQ immunization of hTg mixed with CFA on day 0. Vehicle that was used to dissolve Compound Ia was fed PO to 4 female NOD-DR3 mice as a negative control. Mice were fed again with 250 µg of Compound Ia PO (or vehicle) on day 5 and day 6, followed by SQ immunization of hTg with CFA on day 7. Mice were sacrificed on day 21. Splenocytes and lymph node lymphocytes were isolated and incubated with hTg or Tg.2098 (the major hTg T-cell epitope) to test for their T-cell proliferative responses to these thyroid autoantigens. Splenocytes/lymphocytes were harvested 5 days after stimulation (with hTg) and assayed for T-cell proliferation using the CFSE assay on BD Accuri flow cytometer. Stimulation index was calculated as before. T-cell stimulation in response to hTg was significantly decreased in the group treated with PO Compound Ia (p=0.0285). Response to Tg.2098 also significantly decreased in the group treated PO with Compound Ia (p=0.0147), as shown in Tables 2 and 3:

TABLE 2

| Vehicle plus hTg | Compound Ia plus hTg |
|---|---|
| 1.8 ± 0.2 | 1.0 ± 0.2 |

TABLE 3

| Vehicle plus Tg.2098 | Compound Ia plus Tg.2098 |
|---|---|
| 1.9 ± 0.3 | 0.9 ± 0.1 |

The invention claimed is:

1. A method for treating, forestalling or reducing the risk of autoimmune thyroid disease comprising administering to a patient a compound of formula I

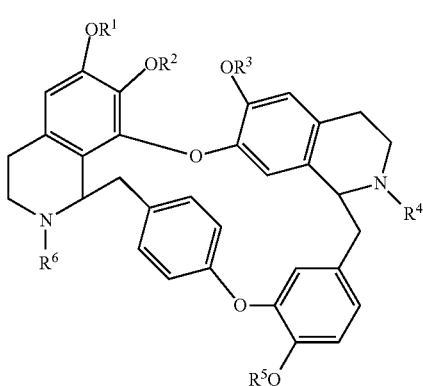

wherein
$R^1$ and $R^2$ are chosen independently from H and $CH_3$, or, taken together $R^1$ and $R^2$ are —$CH_2$—; and
$R^3$, $R^4$, $R^5$, $R^6$ are chosen independently from H and $CH_3$.

2. A method according to claim 1 comprising administering to a patient a compound of formula Ib

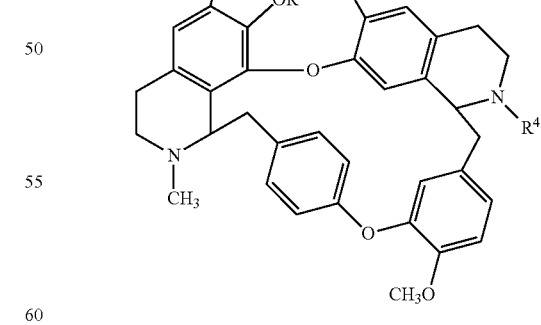

wherein
$R^1$ and $R^2$ are chosen independently from H and $CH_3$, or, taken together $R^1$ and $R^2$ are —$CH_2$—; and
$R^3$ and $R^4$ are chosen independently from H and $CH_3$.

3. A method according to claim 2 wherein said compound of formula I is cepharanthine:

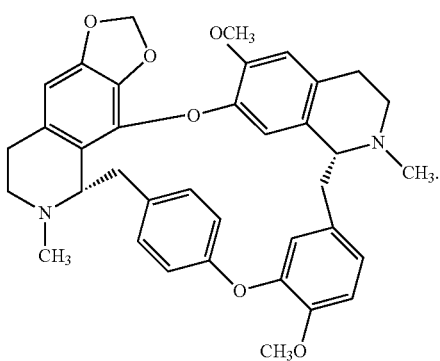

4. A method according to claim 1 wherein said autoimmune thyroid disease is Hashimoto's thyroid disease.

5. A method according to claim 1 wherein said autoimmune thyroid disease is Grave's Disease.

6. A method according to claim 1 wherein said patient carries an HLA-DRβ1-Arg74 variant.

7. A method according to claim 2 wherein said autoimmune thyroid disease is Hashimoto's thyroid disease.

8. A method according to claim 3 wherein said autoimmune thyroid disease is Hashimoto's thyroid disease.

9. A method according to claim 2 wherein said autoimmune thyroid disease is Grave's Disease.

10. A method according to claim 3 wherein said autoimmune thyroid disease is Grave's Disease.

11. A method according to claim 2 wherein said patient carries an HLA-DRβ1-Arg74 variant.

12. A method according to claim 3 wherein said patient carries an HLA-DRβ1-Arg74 variant.

* * * * *

SEQUENCE LISTING

```
<160> NUMBER OF SEQ ID NOS: 5

<210> SEQ ID NO 1
<211> LENGTH: 19
<212> TYPE: PRT
<213> ORGANISM: Homo sapiens

<400> SEQUENCE: 1

Ile Pro Asp Asn Leu Phe Leu Lys Ser Asp Gly Arg Ile Lys Tyr Thr
1               5                   10                  15

Leu Asn Lys

<210> SEQ ID NO 2
<211> LENGTH: 15
<212> TYPE: PRT
<213> ORGANISM: Artificial Sequence
<220> FEATURE:
<223> OTHER INFORMATION: synthetic peptide

<400> SEQUENCE: 2

Leu Ser Ser Val Val Asp Pro Ser Ile Arg His Phe Asp Val
1               5                   10                  15

<210> SEQ ID NO 3
```

```
<211> LENGTH: 15
<212> TYPE: PRT
<213> ORGANISM: Artificial Sequence
<220> FEATURE:
<223> OTHER INFORMATION: synthetic peptide

<400> SEQUENCE: 3

His Asp Leu Phe Ser Arg Ile Asp Ser Ser Val Val Val Val Pro
1               5                   10                  15

<210> SEQ ID NO 4
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 4
cgcttcgaca gcgac                                                   15

<210> SEQ ID NO 5
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 5
gacaaatcca cactccac                                                18
```